(12) United States Patent
Lopaschuk et al.

(10) Patent No.: US 6,727,284 B2
(45) Date of Patent: Apr. 27, 2004

(54) POSTSURGICAL TREATMENT WITH DICHLOROACETATE

(75) Inventors: Gary Lopaschuk, Edmonton (CA); Ruth Collins-Nakai, Edmonton (CA); Koon Teo, Edmonton (CA); Jason R. B. Dyck, Houston, TX (US)

(73) Assignee: University of Alberta (CA)

( * ) Notice: Subject to any disclaimer, the term of this patent is extended or adjusted under 35 U.S.C. 154(b) by 0 days.

(21) Appl. No.: 10/052,453

(22) Filed: Jan. 18, 2002

(65) Prior Publication Data

US 2002/0065318 A1 May 30, 2002

Related U.S. Application Data

(63) Continuation of application No. 09/509,699, filed as application No. PCT/US98/20394 on Sep. 30, 1998, now abandoned.
(60) Provisional application No. 60/060,912, filed on Oct. 3, 1997.

(51) Int. Cl.$^7$ ............................................... A61K 31/19
(52) U.S. Cl. ...................................................... 514/557
(58) Field of Search ........................................ 514/557

(56) References Cited

U.S. PATENT DOCUMENTS

| 5,587,397 A | 12/1996 | Fox ............................ 514/557 |
| 5,643,951 A | 7/1997 | Stacpoole et al. .......... 514/557 |

FOREIGN PATENT DOCUMENTS

| WO | WO 99/17763 | 4/1999 |

OTHER PUBLICATIONS

Beller, et al., "Digitalis intoxication: A prospective clinical study with serum level correlations." *N. Engl. J. Med.* 284:989 (1971).

Bing, et al, "Metabolic studies on the human heart in vivo. Studies on carbohydrate metabolism of the human heart," *Am. J. Med.* 15:284 (1953).

Collins–Nakai, et al., "Dichloroacetic acid (DCA) after open heart surgery in infants and children," Cad. J. Cardiol 11(suppl. E):106E (1995).

Goodman and Gilman's *The Pharmacological Basis of Therapeutics* (Pergamon Press. Eight Edition 1990) (pp. 774–779).

Lopaschuk, et al., "Etomoxir, a carnitine palmitoyltransferase I inhibitor, protects hearts from fatty acid–induced ischemic injury independent of changes in long chain acylarnitine," *Circ. Res.* 63:1036 (1988).

Lopaschuk, et al., "Glucose and palmitate oxidation in isolated working rat hearts reperfused after a period of transient global ischemia," *Circ. Res.* 66:546 (1990).

Lopaschuk, et al., "Plasma fatty acid levels in infants and adults after myocardial ischemia," *Am. Heart J.* 128:61(1994).

McVeigh, et al., "Dichloroacetate stimulation of glucose oxidation improves recovery of ischemic rat hearts," *Am. J. Physiol* 259:H1079 (1990).

Saddik, et al., "Myocardial triglyceride turnover and contribution to energy substrate utilization in isolated working rat hearts," *J. Biol. Chem..* 266:8162 (1991).

Thannikkuto, et al., "Dichloracetate (DCA) stimulates pyruvate dehydrogenase complex (PDC) activity in hearts of patients undergoing coronary artery bypass grafting (CABG)" *Can. J. Cardiol.* 10(suppl. C):130C (1994).

*Primary Examiner*—Zohreh Fay
*Assistant Examiner*—C. Delacroix-Muirheid
(74) *Attorney, Agent, or Firm*—Pillsbury Winthrop LLP

(57) ABSTRACT

A method is described relating to the field of cardiovascular disease and in particular the prevention and treatment of poor cardiac function following surgery. An optimum dose of dichloracetate is described, permitting the continuous maintenance of blood therapeutic levels.

18 Claims, 1 Drawing Sheet

POSTSURGICAL TREATMENT WITH DICHLOROACETATE

PRIOR APPLICATION INFORMATION

This application is a continuation of application Ser. No. 09/509,699, filed Jun. 26, 2000, now abandoned, which is a 371 of PCT US98/20394, filed Sep. 30, 1998, and which claims priority to application Ser. No. 60/060,912, filed Oct. 3, 1997.

FIELD OF INVENTION

The present invention relates to the field of cardiovascular disease and more particularly, the treatment and prevention of poor cardiac function following surgery, including, but not limited to, open heart surgery.

BACKGROUND

Poor cardiac function remains a significant problem in the post-operative period, such as the period following open heart surgery. Drugs used to treat this type of cardiac dysfunction have either forced the heart to work harder (e.g. inotropes), or decreased the work load faced by the heart (e.g. vasodilators, alpha, beta and calcium channel blockers). Unfortunately, both classes of drugs have deleterious side-effects.

For example, one of the most common inotropes used to improve cardiac function is digitalis. However, the dosage of digitalis is critical: intoxication can be fatal. While the overall level of toxicity is not clear, it has been estimated that approximately 25% of hospitalized patients taking digitalis show some signs of toxicity. See Beller et al., "Digitalis intoxication: A prospective clinical study with serum level correlations." N. Engl. J. Med. 284:989 (1971).

Calcium channel blockers also have side-effects. Some, for example, are reported to aggravate myocardial ischemia. This may be due to excessive hypotension or decreased coronary perfusion. See Goodman and Gilman's *The Pharmacological Basis of Therapeutics* (Pergamon Press. Eighth Edition 1990) (pgs. 774–779). While the drug verapamil is less likely to have this problem, the use of the drug is limited. Indeed, it is specifically contraindicated where there are SA or AV nodal conduction disturbances.

What is needed is a safe and effective pharmacological approach to the treatment and prevention of cardiac failure. Such a treatment should permit broad use without significant side-effects.

SUMMARY OF THE INVENTION

The present invention relates to the field of cardiovascular disease and more particularly, the treatment and prevention of poor cardiac function following an ischemic incident, a heart attack, or surgery. With regard to surgery, the procedure can be used before, during and following surgery, and the surgery can be general surgery (e.g., transplantation, such as liver transplantation) or cardiac surgery, such cardiac surgery including, but not limited to, open heart surgery. The present invention relates to new methods of treating poor cardiac performance, such as that resulting from ischemia in a surgical setting. In some embodiments, a patient with a myocardial infarction (e.g., due to occlusion of a coronary artery) is treated by the methods of the present invention.

Both treatment and prevention are contemplated. In one embodiment, the present invention contemplates a method comprising the steps of a) providing: i) a subject having symptoms of poor cardiac performance and ii) means for delivering a solution of dichloroacetate; and b) delivering said solution to said subject with said delivering means under conditions such that said subject has a blood (e.g. serum or plasma) concentration of dichloroacetate in the therapeutic range (such as a concentration of approximately 0.5 mM or greater). In another embodiment, the present invention contemplates a method comprising the steps of a) providing: i) a subject at risk of poor cardiac performance and ii) means for delivering a solution of dichloroacetate; and b) delivering said solution to said subject with said delivering means under conditions such that said subject has a blood (e.g. serum or plasma) concentration of dichloroacetate of greater than approximately 200 $\mu$M, more preferably greater than 500 $\mu$M, and still more preferably greater than 1 mM, for a period of time longer than 1 hour, and more preferably longer than 6 hours, and most preferably 24 hours or longer. In one embodiment, said delivering of step (b) is performed where the conditions comprise a first administration, comprising a bolus, and a second administration, wherein said second administration comprises continuous administration.

It is not intended that the invention be limited to subjects with any one type of symptom of poor cardiac function. Also, the age, sex, or degree of disease state is not intended to be in any way limiting to the present invention, although the invention can be used with particular success on children and infants, including but not limited to neonates.

The invention is also not limited by the cause of poor cardiac function, although the invention can be used with particular success with patients whose cardiac function is poor following surgery, such as open heart surgery. Of course, it is not intended that the present invention be limited to particular surgical procedures. Open heart surgery using cardiopulmonary bypass pump and aortic cross clamp is contemplated as one example of surgery putting patients at risk for poor cardiac function. This includes simple lesions such as a trial septal defect or ventricular septal defect and complex lesions such as transposition arterial switch, Tetralogy of Fallot, atrioventricular septal defect, repair of total veins, Fontan operation, etc. In some embodiments, the methods and composition of the present invention find use in the treatment of myocardial infarction (e.g., during or following thrombolysis). For example, dichloroacetate solution can be supplied during. reperfusion.

While it is not intended that the present invention be limited, by the particular delivery means. One means is an intravenous means, such as that achieved by introduction through an intravenous drip. Other means include (but are not limited to) delivery with a catheter. A preferred means involves direct injection into the aorta.

The particular dosage is also not intended to be limiting. A variety of temporal protocols is contemplated. Delivery in a bolus as well as continuous delivery is contemplated. In a preferred embodiment, dichloroacetate (such as sodium dichloroacetate) is given in a bolus of at least 100 mg/kg of an approximately 100 mg/ml solution (1.0 cc/kg bolus) and, immediately thereafter, dichloroacetate is given as an infusion at approximately 12.5 mg/kg/hr for greater than 10 hours, and more preferably, 24 hours or more.

Higher dosages are permitted. Dichloroacetate does not have significant sideeffects, although some patients experience mild drowsiness.

Definitions

The following definitions are to be used to further explain the invention and should in no way be used to limit the scope of the invention.

"Subject" as used herein refers to a vertebrate. Preferably, the vertebrate is a human.

"Catheter" as used herein refers to a device for insertion into canals, vessels, passageway or body cavities.

"Cardiac disease" as used herein refers to a state in which the heart of a subject is no longer able to function within normal parameters.

"Internally" as used herein refers to the state of being inside the body.

"Temporal protocol" or "dosage regiment" as used herein refers to the time sequence for administration of drug, to i.e. the amount of drug given over time.

DESCRIPTION OF THE INVENTION

Figure 1:
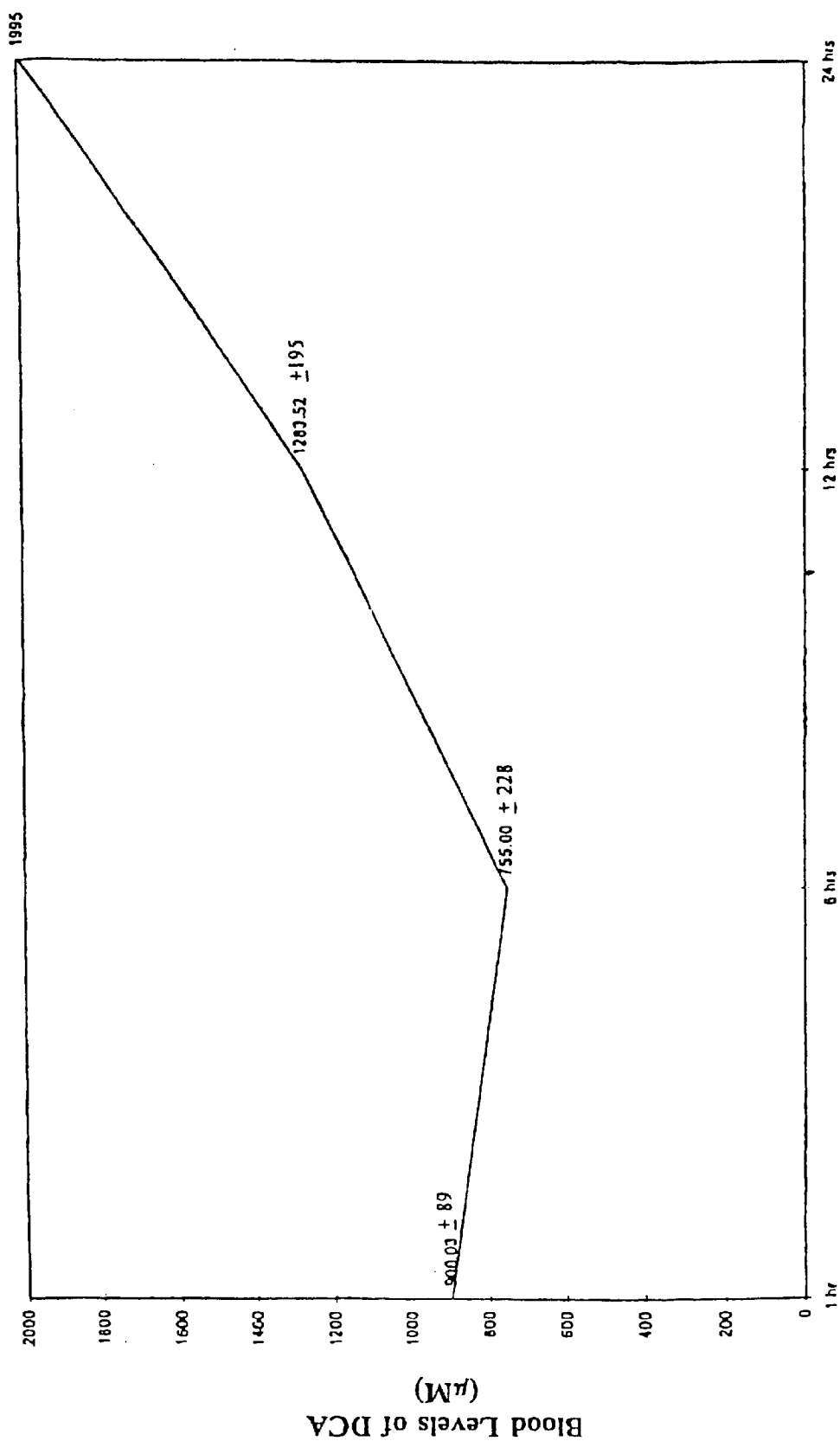
FIG. 1 shows the results of the unique dosage regiment of the present invention, whereby patient blood levels of dichloro acetate are maintained. at high (and therefore therapeutic) levels over a 24 hour period.

The present invention relates to the field of cardiovascular disease and more particularly, the treatment and prevention of poor cardiac function following surgery, including, but not limited to, open heart surgery. One proposed embodiment of the invention contemplates the use of a solution of dichloroacetate (typically sodium dichloroacetate) to reduce or eliminate the morbidity and mortality associated with open-heart surgical techniques, including but not limited to problems associated with the weaning of patients from the heart/lung machine after open heart surgery. The present method of treatment is a substantial improvement over existing techniques because it presents a prevention and treatment approach without significant side-effects.

A. Heart Function

Repetitive Contraction of cardiac muscle requires an efficient and ready source of ATP production to sustain mechanical activity. There are two main mechanisms to produce this ATP in cardiac muscle: 1) glycolysis utilizing glucose as a substrate; and 2) oxidative metabolism utilizing lactate, glucose or fatty acids as substrates.

Glycolysis is an anaerobic process and produces 2ATP per mole of glucose converted to pyruvate. Fatty acid, lactate and glucose oxidation are aerobic processes, that is, requiring oxygen, and produce 129 moles of ATP, 18 moles of ATP and 36 moles of ATP per mole of substrate metabolized, respectively. Bing and colleagues identified that the adult human heart primarily utilizes glucose, lactate and fatty acids as the major sources of energy. See R. J. Bing et al, "Metabolic studies on the human heart in vivo. Studies on carbohydrate metabolism of the human heart," *Am. J. Med.* 15:284 (1953). There is, however, a marked difference in energy substrate utilization between neonatal and adult hearts, with adult hearts preferring fatty acid substrates and newborn hearts more resilient on glucose and lactate as energy substrates.

The type of energy substrate used by the heart can have a profound impact on the ability of the heart to withstand an episode of hypoxia or ischemia. See G. D. Lopaschuk et al., "Etomoxir, a carnitine palmitoyltransferase I inhibitor, protects hearts from fatty acid-induced ischemic injury independent of changes in long chain acylarnitine," *Circ. Res.* 63:1036 (1988). As a result, changes in energy substrate preference during maturation of the heart should influence the outcome of hypoxia or ischemia.

Both hypoxia and ischemia in the immature heart are relevant clinical problems, since hypoxia can occur in the form of birth asphyxia, or with cyanotic congenital heart disease, and ischemia in the setting of surgery to correct congenital heart defects. Differences in myocardial energy substrate utilization may also affect the ability of the newborn heart to withstand ischemia.

Rapid return of myocardial oxidative metabolism is critical for post-operative recovery of ventricular function. The type of carbon substrate oxidized by the heart during reperfusion is also important for recovery. While it is not intended that the present invention be limited to any particular mechanism by which the methods and compositions achieve a therapeutic result, it is believed that increasing glucose oxidation at the expense of fatty acid oxidation will enhance the recovery of previously ischemic myocardium. The beneficial effect of glucose may well result from: 1) an increase in the ratio of ATP produced per oxygen consumed; 2) an increased availability of glycolytically-produced ATP from membrane ion pumps; 3) more rapid return of oxidative metabolism in the immediate reperfusion period; or 4) a decrease in proton production due to an improved coupling between glycolysis and glucose oxidation.

Importantly, glucose is not the primary energy substrate of the heart during perfusion. Under non-ischemic conditions, as noted previously, fatty acids are the primary energy substrate in the adult heart, with glucose oxidation providing only 30 to 40 percent of myocardial ATP production. In experimental studies, it has been demonstrated that glucose oxidation provides an even smaller portion of ATP production in hearts reperfused following period of global ischemia. See G. D. Lopashuk et al., "Glucose and palmitate oxidation in isolated working rat hearts reperfused after a period of transient global ischemia," *Circ. Res.* 66:546 (1990). One of the primary factors resulting in low glucose oxidation rates post-ischemia is the circulating level of fatty acids; serum fatty acids are potent inhibitors of myocardial glucose oxidation.

In patients suffering a myocardial infarction or undergoing heart surgery, serum fatty acids can be markedly elevated. See G.D. Lopasehuk et al., "Plasma fatty acid levels in infants and adults following myocardial ischemia," *Am. Heart J.* 128:61(1994). These high levels of fatty acids have been shown to potentiate ischemic injury in several experimental models including pig, dog, rabbit and rat hearts. See e.g. M. Saddik and G. D. Lopasehuk "Myocardial triglyceride turnover and contribution to energy substrate utilization in isolated working rat hearts," *J. Biol. Chem.* 266:8162 (1991). During and following cardiopulmonary bypass, elevations in fatty acid levels could potentially put the patients at increased risk for prolonged myocardial stunning, manifested by impaired cardiac function, or prolonged inotrope.

B. Reversing Fatty Acid Inhibition

In both aerobic and reperfused ischemic rat hearts, high levels of fatty acids markedly inhibit glucose oxidation rates. This is believed to be the result of marked inhibition by fatty acids of the pyruvate dehydrogenase complex (PDC), a key enzyme complex regulating carbohydrate oxidation.

It is further believed that overcoming fatty acid inhibition of PDC will dramatically increase glucose oxidation and improve functional recovery of ischemic hearts. One of the pharmacologic agents that is particularly effective in reversing fatty acid inhibition of PDC is dichloroacetate. Dichloroacetate (DCA) directly stimulates PDC, resulting in a marked stimulation of glucose oxidation. See J. J. McVeigh and G. D. Lopaschuk "Dichloroacetate stimulation of glucose oxidation improves recovery of ischemic rat hearts,"

*Am. J. Physiol* 259:H1070 (1990). Because infants are noted to have the highest fatty acid levels during and after cardiac surgery, and the lowest rates oxidation for ATP production, it is logical that they may benefit the most from an agent which alters substrate metabolism thus improving not only oxidation but functional recovery. Experimental studies have demonstrated that administration of DCA results in a dramatic stimulation of glucose oxidation during reperfusion of previously ischemic hearts. Again, while an understanding of a precise mechanism is not necessary to the practice of the invention, it is believed that, by selectively stimulating glucose oxidation, secondary to a stimulation of PDC, DCA significantly improves the coupling of glycolysis and glucose oxidation during reperfusion of ischemic hearts. This has the effect of decreasing proton production (H+) due to ATP hydrolysis originating from glycolysis uncoupled from glucose oxidation. By doing so, DCA results in a dramatic improvement in cardiac efficiency during reperfusion, since less ATP is utilized to deal with intracellular ionic in the post-ischemic period.

In adult studies, the present inventors have demonstrated that DCA administration significantly stimulates PDC in heart muscle, strongly suggesting that glucose oxidation is increased. See Thannikkuto et at. "Dichloroacetate (DCA) stimulates pyruvate dehydrogenase complex (PDC) activity in hearts of patients undergoing coronary artery bypass grafting (CABG)" *Can. J. Cardiol.* 10(suppl. C):130C (1994). In a pilot project in which DCA was administered to pediatric patients, the present inventors observed a significant drop in the requirements for inotropes in a immediate post operative period. See R. L. Collins-Nakai et al., "Dichloroacetic acid (DCA) after open heart surgery in infants and children," Cad. J. Cardiol 11(suppl. E):106E (1995).

Unfortunately, due to the very short half-life of dichloroacetate (i.e. approximately 40 minutes), the appropriate dosage regiment for optimum therapeutic effect has not been obtained. The present invention provides methods and compositions that optimize the therapeutic effect of dichloroacetate when used to provide myocardial protection and treatment, during and after cardiac surgery, and in particular, surgery in the pediatric patient. The present invention contemplates that the appropriate regiment for optimum therapeutic effect involves, in part, a longer temporal protocol, i.e. administration for periods longer than 1 hour, and more preferably, longer than 10 hours, and still more preferably 24 hours or more. This is in contrast to single bolus administrations of dichloroacetate which have been found to provide blood levels of the drug in the therapeutic range for less than one hour.

Dichloroacetate is commercially available (typically as a salt). Preparation of the compound and detection of patient levels can be performed using a variety of techniques, such as those discussed in U.S. Pat. No. 5,587,397 to Fox, hereby incorporated by reference.

Experimental

The following example serves to illustrate certain preferred embodiments and aspects of the present invention and is not to be construed as limiting the scope thereof.

EXAMPLE

This example describes the use of dichloroacetate administered in a bolus followed by infusion for 24 hrs in pediatric patients after cardiopulmonary bypass.

Patient Selection:

All patients from newborn to six years of age who require open heart surgery are candidates for administration of dichloroacetate. Neonates are included as they are likely to benefit most from the DCA because of developmental changes in myocardial metabolism. There are no patient contraindications to DCA, but it should be noted that the use of corticosteroids or nicotinic acid in a patient within 24 hrs prior to surgery may change free fatty acid levels. Patients with requirements for insulin or a diagnosis of diabetes can be included, as myocardial function is enhanced in such patients as well. Although insulin requirements may change slightly because of the DCA, in the immediate post-operative period insulin requirements may change dramatically anyway and close observation would be required in such patients.

Oilier Drugs

All procedures and drugs normally given for infants and children undergoing cardiopulmonary bypass are given as routinely administered. Introduction of inotropes in the post-operative period is most easily documented if introduced in a stepwise manner. For purposes of the experiment, both calcium and sodium bicarbonate will be considered to be inotropes, as they both may significantly change the levels of glucose oxidation in the myocardium. Other inotropes to be considered include: epinephrine, dobutamine, dopamine, norepinephrine, phentolamine, phenylephrine and amrinone. The use of other drugs such as vasodilators, diuretics and analgesics or others, are continued as required. Routine post-operative care and management of complications is also contemplated.

Administration of Dichloroacetate

DCA, in a bolus of 100 mg/kg of 10 mg/ml solution (1.0 cc/kg bolus) is injected into the proximal aorta immediately prior to discontinuing the aortic cross-clamp. Immediately thereafter, an infusion of DCA at 12.5 mg/kg/hr is initiated and run for 24 hours or longer. Based on the pharmacokinetics of DCA, this dosage regiment is designed to continuous maintain plasma levels of DCA in the therapeutic range of [0.2–1 mM]—in contrast to transient therapeutic levels.

Measuring Blood Levels

Blood samples are collected from the indwelling lines of patients in citrate-containing tubes. These samples are centrifuged to separate the plasma and frozen. The frozen samples are later analyzed for DCA concentration by using a high performance liquid chromatography technique (HPLC). See generally Thannikkuto et al., "Dichloracetate (DCA) stimulates pyruvate dehydrogenase complex (PDC) activity in hearts of patients undergoing coronary artery bypass grafting (CABG)" *Can. J. Cardiol.* 10(suppl. C):130C (1994). Briefly, the analysis was performed on a IonoSpher A (250×4.6 mm L X ID) column accompanied by a guard column AX. Both of the columns were purchased from Chrompack Canada. The mobile phase used was $10^{-3}$ M pyromellitate buffer (pH 3.8–4.0) at a flow rate of 3.0 mmL/min. Detection was at 320 nm UV. The sample size injected was 20 $\mu$L. The results are shown in FIG. 1. The unique dosage regiment of the present invention clearly results in continuously maintained patient blood levels of dichloroacetate in the therapeutic range. The patients are also observed to require fewer drugs (e.g. inotropes) following surgery (data not shown).

From the above it is clear that the present invention provides a method of treating poor cardiac performance that is both effective and safe. The method results in the need for fewer cardiac performance-enhancing drugs in the first hour after cardiac surgery, and less time on the ventilator and in the intensive care unit. Any further improvements and modifications which become apparent to persons of ordinary skill in the art only after reading this disclosure, the drawings and the following claims are deemed within the spirit and scope of the present invention.

What is claimed is:

1. A method, comprising the steps of:
   a) providing:
      i) a subject having symptoms of poor cardiac performance and
      ii) a solution of dichloroacetate; and
   b) delivering said solution to said subject under conditions which comprise delivery in a bolus followed by continuous administration for a period longer than one hour, such that said subject has a blood concentration of dichloroacetate of approximately 500 $\mu$M or greater for a period of time longer than 1 hour.

2. The method of claim 1, wherein said subject is an adult.

3. The method of claim 1, wherein said subject is a child.

4. The method of claim 1, wherein said subject is an infant.

5. The method of claim 1, wherein said subject is a neonate.

6. The method of claim 1 wherein said subject has undergone cardiac surgery and said delivering of step (b) takes place after surgery.

7. The method of claim 6, wherein said bolus comprises at least 100 mg/kg of an approximately 100 mg/ml solution.

8. The method of claim 7, wherein said continuous administration comprises an infusion at approximately 12.5 mg/kg/hr for greater than 10 hours.

9. The method of claim 8, wherein said delivery results in a blood concentration greater than 1 mM for a period of time longer than 10 hours.

10. A method comprising the steps of:
    a) providing:
       i) a subject at risk of poor cardiac performance and
       ii) a solution of dichloroacetate; and
    b) delivering said solution to said subject under conditions which comprise delivery in a bolus followed by continuous administration for a period longer than one hour, such that said subject has a blood concentration of dichloroacetate of approximately 500 $\mu$M or greater for a period of time longer than 1 hour.

11. The method of claim 10, wherein said subject is an adult.

12. The method of claim 10, wherein said subject is a child.

13. The method of claim 10, wherein said subject is an infant.

14. The method of claim 10, wherein said subject is a neonate.

15. The method of claim 10, wherein said subject has undergone cardiac surgery and said delivering of step (b) takes place after surgery.

16. The method of claim 15, wherein said bolus comprises at least 100 mg/kg of an approximately 100 mg/ml solution.

17. The method of claim 16, wherein said continuous administration comprises an infusion at approximately 12.5 mg/kg/hr for greater than 10 hours.

18. The method of claim 17, wherein said delivery results in a blood concentration greater than 1 mM for a period of time longer than 10 hours.

* * * * *